Figure 5:
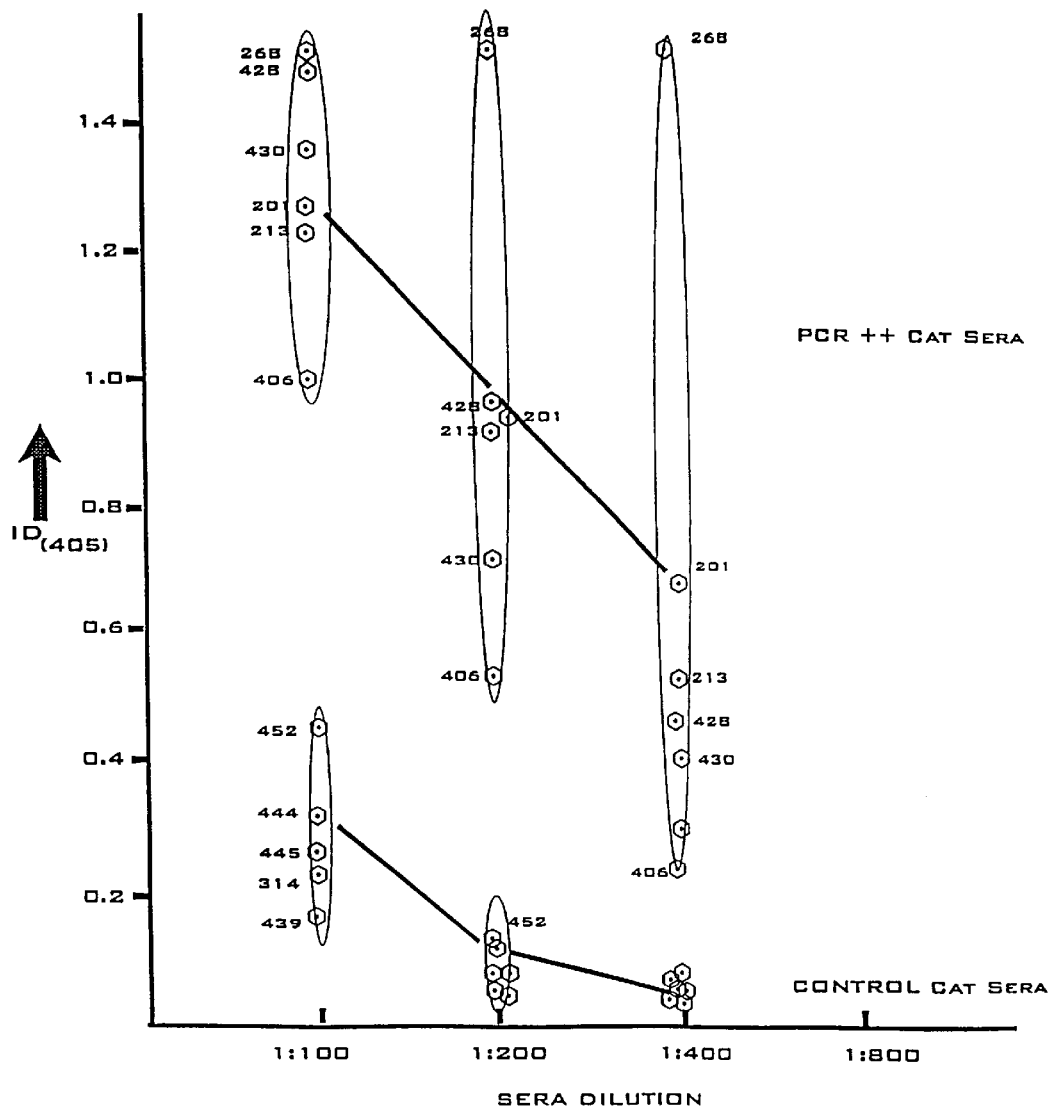

United States Patent [19]
Steele et al.

[11] Patent Number: 6,033,845
[45] Date of Patent: Mar. 7, 2000

[54] SPECIFIC DIAGNOSTIC FOR FELINE INFECTIOUS PERITONITIS ANTIBODIES

[75] Inventors: John Kevin Steele, San Diego; David Louis Telford, Carlsbad, both of Calif.

[73] Assignee: Engene Biotechnologies Inc, Rancho Santa Fe, Calif.

[21] Appl. No.: 08/993,254

[22] Filed: Dec. 18, 1997

Related U.S. Application Data

[60] Provisional application No. 60/033,094, Dec. 18, 1996.

[51] Int. Cl.[7] ............................... C12Q 1/70; G01N 33/50
[52] U.S. Cl. ............................... 435/5; 435/7.1; 435/7.92; 435/7.93; 435/7.94; 536/23.72
[58] Field of Search ............................... 435/69.3, 5, 7.1, 435/7.92–7.94; 424/221.1, 186.1, 204.1; 935/12; 536/23.72

[56] References Cited

U.S. PATENT DOCUMENTS

| | | |
|---|---|---|
| 4,703,001 | 10/1987 | Vodian et al. . |
| 5,037,753 | 8/1991 | Pedersen et al. . |
| 5,118,602 | 6/1992 | Pedersen et al. . |
| 5,232,694 | 8/1993 | Baxendale et al. . |
| 5,246,831 | 9/1993 | Skaletsky et al. . |

FOREIGN PATENT DOCUMENTS

| | | |
|---|---|---|
| 0 264 979 A1 | 4/1988 | European Pat. Off. . |
| 0 310 362 A2 | 4/1989 | European Pat. Off. . |
| 0 376 744 A1 | 7/1990 | European Pat. Off. . |
| 0 386 946 A1 | 9/1990 | European Pat. Off. . |
| 0 411 684 a2 | 2/1991 | European Pat. Off. . |
| WO 87/04624 | 8/1987 | WIPO . |
| WO 92/08487 | 5/1992 | WIPO . |
| WO 93/23421 | 11/1993 | WIPO . |
| WO 95/08575 | 3/1995 | WIPO . |
| WO 96/06934 | 3/1996 | WIPO . |

OTHER PUBLICATIONS

Christianson, K.K. et al., "Characterization of a temperature sensitive feline infectious peritonitis coronavirus", *Arch Virol* 109: 186–196 (1989).

DeGroot, R. J. et al., "cDNA Cloning and Sequence Analysis of the Gene Encoding the Peplomer Protein of Feline Infectious Peritonitis Virus", *J. gen. Virol.* 68: 2639–2646 (1987).

DeGroot, R.J. et al., "Sequence Analysis of the 3' End of the Feline Coronavirus FIPV 79–1146 Genome: Comparison with the Genome of Porcine Coronavirus TGEV Reveals Large Insertions", *Virology* 167: 370–376 (1988).

Fiscus, S.A. et al., "Competitive Enyzme Immunoassays for the Rapid Detection of Antibodies to Feline Infectious Peritonitis Virus Polypeptides", *Journal of Clinical Microbiolgy* 22(2): 395–401 (Sept. 1985).

Abstract, Gambe, D.A. et al., "A Nested Polymerase Chain Reaction Assay for the Detection of Feline Infectious Peritonitis Virus in Clinical Specimens", *PROC. 12th ACVIM Forum* p. 128 (1994).

Herrewegh, A.A.P.M. et al., "Detection of Feline Coronavirus RNA in Feces, Tissues, and Body Fluids of Naturally Infected Cats by Reverse Transcriptase PCR", *Journal of Clinical Microbiology* 33(3): 684–689 (Mar. 1995).

Herrewegh, A.A.P.M. et al., "The Molecular Genetics of Feline Coronaviruses: Camparitive Sequence Analysis of the ORF7a/7b Transcription Unit of Different Biotypes", *Virology* 212: 622–631 (1995).

Ingersoll, J.D. et al., "Comparison of serologic assays for measurement of antibody response to coronavirus in cats", *Am J. Vet. Res.* 49(9): 1472–1479 (Sep. 1988).

Ishida, T. et al., "Feline Infectious Peritonitis Virus Antibody Test Using Enzyme–linked Immunosorbent Assay", *Jpn. J. Vet. Sci.* 49(1): 145–149 (1987).

Kai, K. et al., "A Titration Method of Feline Infectious Peritonitis Virus Using Immunoperoxidase Antibody", *Jpn. J. Vet. Sci.* 50(1): 247–249 (1988).

Pedersen, N.C. et al., "Attempted immunization of cats against feline infectious peritonitis, using avirulent live virus or sublethal amounts of virulent virus", *Am. J. Vet. Res.* 44(2): 229–234 (Feb. 1983).

Siddell, S.G. (Ed), "Feline Infectious Peritonitis", *The Coronaviridae*, ch 14, pp. 293–315 (1995).

Siddell, S.G. (Ed), "Coronavirus Gene Expression", *The Coronaviridae*, ch. 3, pp. 34–54 (1995).

Vennema, H. "Genomic Organization and Expression of the 3' End of the Cannine and Feline Enteric Coronaviruses", *Virology* 191: 134–140 (1992).

Wesseling, J.G. et al., "Nucleotide sequence and expression of the spike (S) gene of canine coronavirus ans comparison with the S proteins of feline porcine coronaviruses", *Journal of General Virology* 75: 1789–1794 (1994).

Hohdatsu, T., et al., "Antigen analysis of feline coronaviruses with monoclonal antibodies (MAbs): Preparation of MAbs which discriminate between FIPV strain 79–1146 and FECV strain 79–1683", *Veternary Microbiology* 28: 13–24 (1991).

*Primary Examiner*—Mary E. Mosher
*Assistant Examiner*—Ali R. Salimi
*Attorney, Agent, or Firm*—Gray, Cary, Ware & Freidenrich LLP; Stephen E. Reiter; Ramsey R. Stewart

[57] ABSTRACT

The present invention is based on the discovery of an antigenic site in the unique 7B polypeptide sequence of Feline Infectious Peritonitis Virus. Specific and sensitive methods for detecting cats infected with Feline Infectious Peritonitis Virus are provided. In particular, methods for determining whether an organism is infected with Feline Infectious Peritonitis Virus comprising providing a peptide or polypeptide including at least one antigenic site from the unique 7B polypeptide therein, contacting the peptide or polypeptide with serum containing antibodies from the organism, and determining whether the antibodies in the serum bind to the peptide or polypeptide. PCR based diagnostics are also provided.

17 Claims, 5 Drawing Sheets

```
79-1146 (SEQ ID 1)           TGTTGGTTGTGTCATACATCATTTGCTGTTGATCTTCCATTTGGGATTCAGATATACCATGA
Applicant's
Sequence(SEQ ID 2)  TGCTTGGTTGTGTCATACATCATTTGCTGTGTCGACCTTCCATTTGGAACTCAGATTTACCATGA
                                  ^10         ^20         ^30         ^40        ^50        ^60

79-1146 (SEQ ID 1)           CAGGGATTTCAACACCCTGTTGATGGCAGACATCTAGATTGTACTCACAGAGTGTACTT
Applicant's
Sequence(SEQ ID 2)  CAGGGATTTCCAAAACCCTGTTAATGGTAGGCATCTAGAGTGTACTCACAGAGTTACTT
                                  ^70         ^80         ^90         ^100       ^110       ^120

79-1146 (SEQ ID 1)           TGTGAAGTACTGTCCACATAACCTGCATGGTTATTGCTTTAATGAGAGGCTGAAAGTTTA
Applicant's
Sequence(SEQ ID 2)  TGTGAAGTACTGTCCATACAACCTGCATGGTTATTGCTTTAATGAGAAGCTGAAAGTTCA
                                  ^130        ^140        ^150        ^160       ^170       ^180

TGACTTGAAGCAATTCAGAAGCAAGAAGGTCTTCGACAAAATCAACCAACATCATAAA
                    TAACTTGATGCAACTTAGAAGCAAGAAGGTTTTTGACAAGATCAACCAACATCATTAA
                                  ^190        ^200        ^210        ^220       ^230
```

FIG. 1

87.2% identity in 78 aa overlap

```
              10v        20v        30v        40v        50v
79-1146 (SEQ ID 3)  VGCHTSFAVDLPFGIOIYHDRDFOHPVDGRHLDCTHRVYFVKYCPHNLHGY
Applicant's
Sequence(SEQ ID 4)  VGCHTSFAVDLPFGTQIYHDRDFQNPVNGRHLECTHRVYFVFVKYCPYNLHGY
              10^        20^        30^        40^        50^

60v        70v
79-1146 (SEQ ID 3)  CFNERLKVYDLKQFRSKKVFDKINQHHK
Applicant's
Sequence(SEQ ID 4)  CFNEKLKVHNLMQLRSKKVFDKINQHH
              60^        70^
```

Optimized score is 407

FIG. 2

SUMMARY DATA ON APPLICANTS SEQUENCE

RESIDUES ANALYZED:     78              WINDOW SIZE:  KYTE  9
                                                     HOPP  7

FIRST PASS MADE:  YES                  pH:   7.000

ROBSON                                 CHOU-FASMAN
CONFORMATION:   HELIX      36%         CONFORMATION:  HELIX     33%
                EXTENDED:  40%                        EXTENDED  86%
                TURN:      19%                        TURN      28%
                COIL        6%

Robson Decision Constants:
HELIX  EXTEND  TURN  COIL
 -75    -88     0     0

ANTIGENIC SITES:  COORDINATE    KYTE INDEX
                      22           2.42
                      24           1.84
                      23           1.81
                      76           1.81
                      18           1.79

MOLECULAR WT:  OTAL   9334 g/mol   AVE HYDROPHOBICITY:  KYTE (100X)  -61
               AVERAGE 120 g/mol                        HOPP (-100X)  15

ISOELECTRIC PT:  pH= 8.77

AMINO ACID DISTRIBUTION:

| RESIDUE  | NUMBER | PERCENT | RESIDUE  | NUMBER | PERCENT |
|----------|--------|---------|----------|--------|---------|
| Ala (A)  | 1      | 1%      | Phe (F)  | 6      | 8%      |
| Arg (R)  | 4      | 5%      | Pro (P)  | 3      | 4%      |
| Asn (N)  | 6      | 8%      | Ser (S)  | 2      | 3%      |
| Asp (D)  | 4      | 5%      | Thr (T)  | 3      | 4%      |
| Cys (C)  | 4      | 5%      | Trp (W)  | 0      | 0%      |
| Glu (E)  | 2      | 3%      | Tyr (Y)  | 5      | 6%      |
| Gln (Q)  | 4      | 5%      | Val (V)  | 7      | 9%      |
| Gly (G)  | 4      | 5%      | Asx (B)  | 0      | 0%      |
| His (H)  | 8      | 10%     | Glx (Z)  | 0      | 0%      |
| Ile (I)  | 2      | 3%      | Ter (.)  | 0      | 0%      |
| Leu (L)  | 6      | 8%      | Xxx (X)  | 0      | 0%      |
| Lys (K)  | 6      | 8%      | ??? (?)  | 0      | 0%      |
| Met (M)  | 1      | 1%      |          |        |         |

FIG. 3

SUMMARY DATA ON PUBLISHED SEQUENCE

RESIDUE ANALYZED:        78              WINDOW SIZE:    KYTE   9
                                                         HOPP   7
FIRST PASS MADE:    YES                  pH:    7.000

ROBSON                                   CHOU-FASMAN
CONFORMATION: HELIX:       33%           CONFORMATION:  HELIX      26%
              EXTENDED:    41%                          EXTENDED   78%
              TURN         22%                          TURN       28%
              COIL          5%

Robson Decision Constants:
HELIX   EXTEND   TURN   COIL
 -75      -88      0      0

ANTIGENIC SITES:   COORDINATE    KYTE INDEX
                       22           2.39
                       65           1.93
                       24           1.81
                       76           1.81
                       23           1.78

MOLECULAR WT: TOTAL    9417 g/mol  AVE HYDROPHOBICITY: KYTE (100X) -64
              AVERAGE   121 g/mol                      HOPP (-100X)  6

ISOELECTRIC PT:  pH= 8.50

AMINO ACID DISTRIBUTION:

| RESIDUE  | NUMBER | PERCENT | RESIDUE  | NUMBER | PERCENT |
|----------|--------|---------|----------|--------|---------|
| Ala (A)  | 1      | 1%      | Phe (F)  | 7      | 9%      |
| Arg (R)  | 5      | 6%      | Pro (P)  | 3      | 4%      |
| Asn (N)  | 3      | 4%      | Ser (S)  | 2      | 3%      |
| Asp (D)  | 7      | 9%      | Thr (T)  | 2      | 3%      |
| Cys (C)  | 4      | 5%      | Trp (W)  | 0      | 0%      |
| Glu (E)  | 1      | 1%      | Tyr (Y)  | 5      | 6%      |
| Gln (Q)  | 4      | 5%      | Val (V)  | 7      | 9%      |
| Gly (G)  | 4      | 5%      | Asx (B)  | 0      | 0%      |
| His (H)  | 9      | 12%     | Glx (Z)  | 0      | 0%      |
| Ile (I)  | 3      | 4%      | Ter (.)  | 0      | 0%      |
| Leu (L)  | 5      | 6%      | Xxx (X)  | 0      | 0%      |
| Lys (K)  | 6      | 8%      | ??? (?)  | 0      | 0%      |
| Met (M)  | 0      | 0       |          |        |         |

FIG. 4

SPECIFIC DIAGNOSTIC FOR FELINE INFECTIOUS PERITONITIS ANTIBODIES

RELATED APPLICATIONS

The present application claims priority from U.S. Provisional Patent Application Ser. No. 60/033094, filed Dec. 18, 1996.

BACKGROUND OF THE INVENTION

The coronaviruses are a large group of viruses including hundreds of individual species. A wide range of hosts, including humans, mice, cows, pigs, dogs, turkeys, and cats are susceptible to coronavirus infection.

There are 10–20 different coronaviruses capable of infecting cats. Among the feline coronaviruses are Feline Infectious Peritonitis Virus (FIPV) and Feline Enteric Coronavirus (FECV). Currently, there is considerable academic debate over whether FIPV and FECV are two distinct species of coronavirus, or whether they are merely strain variations within the same coronavirus species.

Under one theory, FIPV and FECV are distinct species which are responsible for different disease states. According to this theory, FIPV infection may be manifested through either of two types of pathologies. The first form, called the wet or effusive form, results from a massive immune response against the infecting coronavirus during which ascites fluid appears in the animal's coelomic cavity. The effusive form of the disease progresses rapidly and is inevitably fatal.

The second form of the disease, called the dry form, is the consequence of a more effective response of the immune system to the presence of coronavirus infected cells. There is, at first, a localized inflammation with a subsequent "walling off" of the infected cells. This effect generates a nodule, which may occur in various parts of the body. The dry form of the disease may or may not be fatal depending on the localization of the nodule. For example, nodulation within the brain may prove rapidly fatal, whereas nodulation within muscle or the peritoneal wall may be tolerated for prolonged periods.

Regardless of whether the infected cat exhibits the effusive pathology or the dry pathology, once infected, a cat remains infected and is a carrier of the virus for the remainder of its life. The infected cat can transmit the virus to other cats with which it comes in contact. Thus, it is desirable to detect cats capable of transmitting the potentially lethal virus in order to prevent the spread of the disease.

According to the theory holding that FIPV and FECV are distinct species, FECV is responsible for a mild intestinal disorder. FECV infection may or may not result in diarrhea, but is self limiting in either case. Thus, cats infected with FECV completely recover from the infection.

Under the second theory, FIPV and FECV are strain variants within the same species and the pathology exhibited by the infected cat, whether the wet form, the dry form, or enteric disease, is determined by host factors.

Cats exposed to any coronavirus capable of infecting them produce antibodies against generic epitopes common to these coronaviruses. A currently available diagnostic quantitates the levels of antibodies directed against these generic epitopes. Such assays risk misdiagnosis because exposure to any coronavirus can generate an immune response in the cat and thereby yield a positive result in the assay.

Thus a need exists for an assay capable of discriminating between potentially fatal coronaviruses and those which do not pose a significant threat.

Another currently available assay utilizes PCR to detect infection with FIPV. However, in some cases, FIPV infected cats may not yield a positive result in the PCR assay due to the sequestration of the virus in limited regions of the host's body or to differences between the sequences of the primers used in the PCR analysis and the sequence of the viral DNA. Consequently, a need exists for diagnostics which have even greater sensitivity than the PCR based methods. In addition, a need exists for improved PCR based diagnostics which provide increased detection levels relative to those currently available.

SUMMARY OF THE INVENTION

The present invention relates to diagnostics for detecting cats infected with Feline Infectious Peritonitis Virus. The invention is based on the discovery of an antigenic site in the unique 7B polypeptide of Feline Infectious Peritonitis Virus.

One aspect of the invention is a method for determining whether an organism is infected with Feline Infectious Peritonitis Virus. The method comprises the steps of providing a peptide or polypeptide including at least one antigenic site from the unique 7B polypeptide therein, contacting the peptide or polypeptide with serum containing antibodies from the organism, and determining whether the antibodies in the serum bind to said peptide or polypeptide, wherein detection of binding of said antibodies to said peptide or polypeptide indicates that the organism is infected with Feline Infectious Peritonitis Virus.

In one embodiment of the above method, the peptide or polypeptide includes at least one antigenic site from SEQ. ID. NO: 4 (the unique 7B polypeptide sequence of Applicant' field isolate of FIPV) therein.

In another embodiment of the method, the determining step comprises contacting the antibodies from the serum with a second antibody. The second antibody is capable of providing a detectable signal. The presence of the signal indicates the presence of antibodies directed against the peptide or polypeptide in said serum.

In one embodiment, the second antibody is linked to an enzyme capable of providing a detectable signal. In another embodiment, the second antibody is labelled with a radioactive isotope.

In one embodiment of the method, the peptide or polypeptide containing at least one antigenic site from the unique 7B polypeptide is coated on a surface. In another embodiment, the surface is a microtiter plate.

Another aspect of the invention is a method for detecting the presence of immune cells which replicate in response to a peptide or polypeptide having at least one antigenic site from the sequence of SEQ. ID. NO: 4. The method comprises the steps of obtaining immune cells from an organism, contacting said immune cells with a peptide or polypeptide having at least one antigenic site from the sequence of SEQ. ID. NO: 4 therein or with a control solution lacking said peptide or polypeptide, and comparing the replication of said immune cells contacted with said peptide or polypeptide to the replication of said immune cells contacted with said control solution, wherein increased replication in the cells contacted with said peptide or polypeptide relative to the cells contacted with the control solution indicates the presence of immune cells responsive to said peptide or polypeptide.

In one embodiment of the above method for detecting the presence of immune cells which replicate in response to a peptide or polypeptide having at least one antigenic site from the sequence of SEQ. ID. NO: 4, the immune cells are T cells.

In another embodiment of the method for detecting the presence of immune cells which replicate in response to a peptide or polypeptide having at least one antigenic site from the sequence of SEQ. ID. NO: 4, replication is measured by determining the number of colonies on a plate.

Another aspect of the invention is a method of detecting the presence of antibodies directed against a peptide or polypeptide having at least one antigenic site from the sequence of SEQ. ID. NO: 4 therein comprising the steps of labelling the peptide or polypeptide, contacting the peptide or polypeptide with an antibody directed against an antigenic site from SEQ. ID. NO: 4, adding varying amounts of sera from said organism to the mixture comprising the labelled peptide or polypeptide and said antibody, and comparing the amount of labelled peptide or polypeptide bound to the antibody in the samples containing varying amounts of the serum to the amount of labelled peptide or polypeptide bound to the antibody in a control sample lacking the 7B protein, wherein decreased binding in the samples containing the serum relative to the control sample indicates the presence of a peptide or polypeptide containing an antigenic site from the sequence of SEQ ID NO: 4 in the serum.

Another aspect of the present invention is a method for determining whether an organism is infected with Feline Infectious Peritonitis Virus comprising the steps of obtaining a DNA sample from the organism, and performing a polymerase chain reaction analysis on the DNA sample in which at least one of the primers comprises a sequence contained within SEQ ID NO:2. The at least one primer has at least one nucleotide which differs between SEQ ID NO:2 and SEQ ID NO: 1. The presence of an amplified fragment indicates that the organism is infected with Feline Infectious Peritonitis Virus.

In one embodiment of the PCR method, two primers comprising sequences contained within SEQ ID NO:2 are used, each primer having at least one nucleotide therein which differs between SEQ ID NO:2 and SEQ ID NO: 1. In this embodiment, the primers may have the sequences of SEQ ID NO:5 and SEQ ID NO:6.

Another aspect of the present invention is a method of inducing an immune response against FIPV in an animal comprising administering a dose of the 7B protein or a portion thereof having at least one antigenic site therein to an animal which is sufficient to induce a desired level of immune response against FIPV. In one embodiment of the method, the portion of the 7B protein comprises at least 10 consecutive amino acids of the 7B protein. In another embodiment of the method, the portion of the 7B protein comprises at least 10 consecutive amino acids of the sequence of SEQ ID NO:3. In a further embodiment of the method, the portion of the 7B protein comprises at least 10 consecutive amino acids of the sequence of SEQ ID NO:4.

BRIEF DESCRIPTION OF THE DRAWINGS

FIG. 1 is a comparison of the published sequence of the unique 7B DNA sequence of FIPV strain 79-1146 (SEQ. ID. NO:1) with that of the unique 7B DNA sequence of Applicant's field isolate of FIPV (SEQ. ID. NO:2).

FIG. 2 is a comparison of the amino acid sequence encoded by the unique 7B DNA sequence of FIPV strain 79-1146 (SEQ. ID. NO:3) and that encoded by the unique 7B DNA sequence of Applicant's field isolate (SEQ. ID. NO:4).

FIG. 3 shows the Kyte index of the polypeptide of SEQ. ID. NO:4.

FIG. 4 shows the Kyte index of the polypeptide of SEQ. ID. NO: 3.

FIG. 5 is a comparison of the results of ELISA assays conducted on cats which were positive for FIPV by PCR to those of cats which were negative for FIPV by PCR.

DETAILED DESCRIPTION OF THE PREFERRED EMBODIMENT

The present invention is based upon the discovery of an antigenic epitope within the 7B gene of FIPV. The 7B gene is a virulence factor which must be present in order for the virus to cause lethal disease. In fact, there are some reports that immune responses directed against the 7B polypeptide are responsible for the fatality of the wet form of the disease.

Furthermore, viruses in which the 7B gene is deleted are incapable of causing lethal disease and have been used as nonpathogenic vaccines against FIPV. Additional support for the role of the 7B gene in influencing viral virulence came from the observation that an FECV strain having a deletion within the 7B gene was incapable of causing lethal disease. Vennema et al., *Genomic Organization and Expression of the* 3' *End of the Canine and Feline Enteric Coronaviruses*, Virology 191:134–140 (1992)). As virulence factors have often been employed as protective immunogens in vaccines, the 7B gene may be used to induce protective immunity in animals.

The above observations sparked the hypothesis that FECV and FIPV were distinct viral strains distinguishable by the presence of this sequence (hereinafter called the unique 7B DNA sequence) in the 7B gene of FIPV and the absence of the unique 7B DNA sequence in the 7B gene of FECV. According to this hypothesis, FECV was incapable of causing lethal disease by virtue of the deletion of the unique 7B DNA sequence in its 7B gene. However, other reports have characterized strains as FECV despite the fact that they contain the unique 7B DNA sequence within their 7B genes, leading to the debate over whether FECV and FIPV are distinct species which are the causative agents of distinct disease states. As used herein, the designation FIPV refers to viruses having the unique 7B DNA sequence in their 7B gene and the designation FECV refers to viruses lacking the unique 7B DNA sequence in their 7B genes.

Despite the debate over whether FIPV and FECV are different species distinguishable by the unique 7B DNA sequence within the 7B gene, it is clear that viruses possessing the unique 7B DNA sequence are associated with potentially lethal disease. Therefore, diagnostics based on the detection of the sequence within the 7B gene are capable of distinguishing cats infected with a virus capable of causing lethal disease from cats infected with nonlethal viruses and uninfected cats.

Although a number of other approaches for detecting coronavirus infected cats capable of transmitting a lethal disease have been attempted, the present diagnostics based on the antigenic epitope in the 7B gene provide significant advantages over these approaches.

One of the attempted approaches is based on differential titers of antibodies directed against generic epitopes common to all feline coronaviruses. In this approach, generic feline coronavirus antigens are used to bind generic anti-coronavirus antibodies in blood, serum or ascites fluid of a cat. The levels of these generic anti-coronavirus antibodies are then quantitated. Since the wet form of feline infectious peritonitis results in very high titers of these generic anti-coronavirus antibodies, cats with high titers of generic coronavirus antibodies are presumed to have been infected with a lethal feline coronavirus, while those with low titers are presumed to have been infected with a non lethal virus. This assay is prone to both false positives and false negatives because early in infection with a lethal feline coronavirus a cat may have low generic antibody titers, while a cat shortly after recovery from an infection with a non-lethal virus may have elevated generic antibody titers. Because of these limitations, the utility of this approach is restricted to confirmation of clinical diagnosis and postmortem analyses when death is suspected to be due to FIPV. The value of this approach as a specific diagnostic is low.

Another approach is a PCR based diagnostic in which the unique 7B DNA sequence is amplified. Detection of the unique 7B DNA sequence by PCR is indicative of infection with a potentially lethal virus. The PCR based diagnostic has been used to confirm clinically-diagnosed cases of FIP. To date approximately 2000 tests have been performed with approximately 1000 follow-ups. Results have been found to have a positive predictive value approaching 100%. However, the PCR based assay is susceptible to false negatives resulting from the fact that the virus may be spatially sequestered in the body of the host. Consequently, the sample on which the PCR analysis is performed may lack viral nucleic acid even when the animal is infected with a virus possessing the unique 7B DNA sequence, thereby resulting in a false negative. The present invention provides increased sensitivity in the detection of potentially lethal viral strains.

The present invention evolved from Applicant's development of an improved PCR based diagnostic for FIPV having higher detection rates than the presently available PCR diagnostics. During the development of the improved PCR based diagnostic, Applicant determined the sequence of the unique 7B DNA sequence from a clinically diagnosed FIPV case obtained from the field. FIG. 1 compares the published sequence of the unique 7B DNA sequence of FIPV strain 79-1146 (SEQ. ID. NO:1) with that of the unique 7B sequence of Applicant's field isolate of FIPV (SEQ. ID. NO:2). The sequence shown in FIG. 1 extends between base pair 751 through base pair 988 of the FIPV genome. As shown in FIG. 1, the sequence determined by Applicant has an overall identity of 89% with the published sequence.

Viruses having the sequence of SEQ. ID. NO:2 are common in the field as evidenced by the increased FIPV detection rates when primers incorporating the sequence differences between SEQ. ID. NO:1 and SEQ. ID. NO:2 were employed in the PCR diagnostic the FIPV detection rate improved. In a small study, the FIPV detection rate in cats increased from 3/10 to 5/10. Therefore, improved diagnostics can be obtained by exploiting the sequence of the unique 7B sequence disclosed herein. In such improved PCR diagnostics, primers may be used which reflect the sequence differences between Applicant's unique 7B DNA sequence, SEQ ID NO: 2 and the published unique 7B DNA sequence, SEQ ID NO:1.

FIG. 2 is a comparison of the amino acid sequence encoded by the unique 7B DNA sequence of FIPV strain 79-1146 (SEQ. ID. NO:3) and that of Applicant's field isolate (SEQ. ID. NO:4). As shown in FIG. 2, there are 10/78 amino acid residues that are different (87% homology) between the polypeptide, hereinafter called the unique 7B polypeptide, encoded by each of the DNA sequences.

These amino acid differences altered the antigenicity of sequences within the unique 7B polypeptide as measured by the Kyte index. FIG. 3 shows the Kyte index of the polypeptide of SEQ. ID. NO:4. FIG. 4 shows the Kyte index of the polypeptide of SEQ. ID. NO: 3. As demonstrated in FIGS. 3 and 4, the polypeptide of SEQ ID NO:4 and the published polypeptide from strain 79-1146 (SEQ ID NO:3) both have two similar antigenic regions as determined by the Kyte Index. There is a strong antigenic region extending from amino acid 22 to 24, and a less strng antigenic determinant at amino acid 76. However, there is an additional antigenic determinant at amino acid 18 in the sequence of SEQ ID NO:4 that is not found in the corresponding region of the sequence of SEQ ID NO:3.

Based on the results of the computer based antigenicity analysis of Applicant's 7B sequence, the actual antigenicity of the unique 7B polypeptide was evaluated experimentally. In this analysis, the unique 7B polypeptide of SEQ. ID. NO: 4 was expressed in bacteria as a fusion protein with the maltose binding protein (MBP).

EXAMPLE 1

Construction of the pMAL Expression Vector

A region corresponding to base pair 751 through 988 of the FIPV genome was cloned into the pMAL™-2 vector (New England BioLabs, Catalog #800, Version 3.02) such that the unique polypeptide was in frame with the maltose binding protein. The pMAL vector was constructed as follows.

a. cDNA Synthesis

Two µg of total RNA isolated from the mesenteric lymph node of a clinical FIP case ("Buck" Leitner) was added to a tube containing 1 µl Random Hexamer primers obtained from Gibco. The solution was heated to 70 degrees to denature the mRNA, then cooled to 4 degrees on ice to anneal the primers to the mRNA. Reverse transcriptase (2 µl MMLV RT, Promega, Inc., was added, and the mixture was incubated for 10 min at 25°, 50 min at 42° and 15 min at 70°. Finally, RNase H (Gibco) was added to degrade remaining RNA and the mixture was incubated for 20 min at 37° C. Next, the cDNA containing the 7B gene generated by this reaction was amplified by PCR as described below.

b. PCR Reaction Method cDNA containing the 7B gene was specifically amplified by PCR as follows. The primer sequences utilized in the PCR reaction were:

5-prime: TGTTGGTTGTCATACATCATTTG (SEQ. ID. NO:5)

3-prime: CTCAGTTTAATGATGTTGGTTG (SEQ. ID. NO:6)

The oligonucleotide primers were added at a concentration of 0.1 mg/ml in $H_2O$ to 3 µl cDNA from above. The PCR reaction was run according to standard methods using 2.5 units of Taq (Promega) and 200 µM of each dNTP solution (Gibco). The reaction profile employed was:

| Time | Temp | Cycles |
| --- | --- | --- |
| 2.5 min | 94 | 1 |
| 0.5 min | 94 | |
| 1.5 min | 55 | 30 |
| 1.0 min | 72 | |
| 10 min | 72 | 1 | c. Purification of PCR Product

The DNA from 10 individual PCR reactions as above were pooled and organically extracted once with Phenol/Chloroform/Isoamyl alcohol to denature the Taq DNA polymerase. DNA was precipitated from the mix by standard methods employing 100% Ethanol at −20°.

The DNA was sized on a 2.5% Agarose gel and the PCR product was purified as follows. The PCR product was detected by UV florescence, cut out with a razor blade, and purified using glass milk. The concentration of the purified DNA was determined by spectrophotometric analysis at 260 nm.

d. Ligation into pCRII Cloning Vector

The PCR product was inserted into the pCRII cloning vector. The ligation reaction was run according to the manufacturers' protocol. The pCRII vector is supplied open, with a terminal "T" nucleotide at each end. The PCR product above has terminal "A" nucleotides added by the natural action of Taq. The amount of PCR product included in the ligation reaction was determined using the following formula:

$$\text{Xng PCR product needed} = \frac{243\text{bp PCR product} \times 50\text{ng pCRII vector}}{3900\text{bp pCRII vector}}$$

Therefore, 3.11 ng of 7B PCR product was added at 270 ng/μl to 50 ng of PCRII vector. The ligation reaction was incubated overnight at 14° C.

The ligation mixture resulting from the above procedure was transformed into chemically competent *E. coli* cells according to the manufacturers' protocol. Thereafter, 3 μl mercaptoethanol and 3 μl Ligation reaction were added to 50 μl *E. coli*, and incubated for 30 minutes on ice. The cells were then heat shocked for 30 seconds at 42° C., and returned to ice for 2 minutes.

The cells were incubated in Luria broth for 60 minutes at 37° C., plated on LB-agar plates with Ampicillin and X-gal, and incubated overnight at 37° C. After incubation, white colonies in which the lac gene had been disrupted by inserted DNA were picked, and grown up overnight. e. Preparation of pMAL-2 Expression Vector Encoding the 7B-maltose Binding Protein Fusion Protein The pMAL-C2 vector was prepared for cloning as follows: 3 μg vector was cut with 30 units of the restriction endonuclease EcoRI (Boeringer Mannheim) for 1.5 hours at 37° C. The 7B insert in the pCRII construct made above was excised by digesting 5 ug 7B-pCRII construct with 10 units of EcoRI for 1 hour at 37° C.

The desired restriction fragments were purified by agarose gel electrophoresis.

The digested pMAL-C2 vector was dephosphorylated with 2U alkaline phosphatase (Boeringer Mannheim) for 60 minutes at 37° C. then 1 μl 500 mM EDTA added with a further 60 minutes of incubation at 65° C. The resulting mixture was organically extracted with Phenol/Chloroform/Isoamyl alcohol and ethanol precipitated. The dephosporylated cut vector was then gel purified as above.

The ligation reactions were run at a 1:1 and at a 1:4 molar ratio of vector to insert with 1 μl T4DNA Ligase enzyme (4U), and incubated overnight at 14° C. Both preparations were transformed into chemically competent *E. coli* cells using the method detailed above.

Clones resulting from the ligation reactions above were chosen, grown up, and subjected to restriction analysis by digestion of the plasmid DNA with XbaI restriction endonuclease. Clones with the DNA in the correct forward orientation gave a 162 bp band by electrophoresis; plasmids with the DNA in the incorrect orientation gave a 105 bp band. Incorrect clones were discarded, and a correct clone selected for protein expression.

EXAMPLE 2

Expression and Purification of Protein

Bacteria containing the pMAL vector encoding the 7B-maltose binding protein fusion protein were grown at 37° C. in a 500 ml culture; When the OD of the culture at 600 nm reached 1.0, 1 gram of glucose and 1.5 ml 100 mM IPTG were added and the mixture induced for 2 hours at 37° C. Cells were pelleted, washed 2× in 4° C. PBS; Thereafter, the cells were resuspended in 20 mls Tris-EDTA with 50 ul of a 100 mg/ml Pefabloc (Boeringer Mannheim) protease inhibitor solution added. Cells were freeze/thawed 3× in liquid nitrogen and a 20° C. water bath, then sonicated on ice for 2 minutes and centrifuged at 15,00 g for 5 minutes. Supernatant was loaded onto a 1 ml Amylose resin column with Tris-EDTA buffer and washed until the OD 280>>0.00. The 7B-maltose binding protein fusion protein was eluted with 10 mM maltose, and 1 ml fractions collected and stored.

Following purification, the antigenicity of the polypeptide encoded by the 237 bp fragment was evaluated by Western blotting.

EXAMPLE 3

SDS-PAGE gel and Western Blot Analysis

In order to visualize the resulting protein, samples were run on SDS-PAGE electrophoresis gels. Briefly, 100 μl of protein-positive fractions from above were suspended in Reducing Sample Buffer (Tris-glycine/2-mercaptoethanol/glycine), boiled for 2 min, and run on a 13% acrylamide gel along with a maltose binding protein control and molecular weight markers. Proteins were visualized with 2% Coomassie blue solution, destained with 30% methanol, 10% Acetic Acid, 60% water solution. A protein band having a molecular weight of approximately 65 kD was observed in samples obtained from cells containing the 7B-maltose binding protein expression vector. This band was at the expected molecular weight for the 7B-maltose binding protein.

Western blots were run by transferring the above gels to PVDF Immobilon matrix in Tris-glycine/10% Methanol transfer buffer at 200 mA for 2 hours. The blots were blocked with 20 g/200 ml PBS skim milk powder at 4° C. overnight and cut into strips. Each strip was incubated with sera from FIPV infected or uninfected cats diluted 1:100 in PBS/0.05% Tween 20 solution for 1 hour at room temp. The blots were washed 3× in PBS/Tween, and incubated with Protein-A-colloidal gold conjugate (Sigma corp) diluted 1:1000 in PBS-Tween for 1 hour. The blots were then washed, dried and stored.

A band having a molecular weight of approximately 65 kD, the expected molecular weight of the 7B-maltose binding protein fusion protein, was detected with serum from an FIPV infected cat but not with serum from the control cat. The antigenicity of the unique polypeptide observed in the Western blots demonstrates that the unique polypeptide may be used in diagnostic assays to distinguish between cats infected with FIPV and FECV.

EXAMPLE 4

T cell Stimulation Assay

A further indication of the antigenicity of the unique peptide was observed with an in vitro T-cell stimulation assay. White blood cells (WBC's) were prepared by Ficoll gradient purification from 10 ml of whole blood obtained from a cat known to have clinical FIP (cat #88). The cells were resuspended in 1 ml of RPMI medium, supplemented with glutamine and 20% bovine fetal serum. 100 μL samples of this suspension was then dispensed into each of 8 microplate wells. In addition, one of the following was added to separate pairs of wells: 20 μg/ml of purified 7B conjugate, 10 μg/ml of purified 7B conjugate, MBP alone, or medium alone. After two days of incubation, developed colonies were counted and recorded photographically. The number of colonies observed for each sample is listed in table I below.

TABLE I

T-Cell Colony Stimulation by 7B Peptide

| Treatment | 1st well | 2nd well | mean | mean less control |
|---|---|---|---|---|
| serum only control | 21 | 19 | 20 | — |
| MBP control | 18 | 20 | 19 | −1 |
| 10 μg/ml 7B | 27 | 32 | 30 | 10 |
| 20 μg/ml 7B | 45 | 57 | 51 | 31 |

No. of Colonies

These experiments demonstrate that for the cat investigated, MBP is not a significant antigen that upregulates memory T-cells. Furthermore, in contrast to the lack of antigenicity observed with MBP, a 7B peptide concentration-dependent upregulation of memory T-cells was observed. These results indicate that an FIPV-infected cat has specific memory T-cells for the unique peptide and that the unique peptide may be used in a cell-based assay to specifically diagnose FIPV infection. Additionally, these experiments demonstrate that the unique peptide may be used in other assays, such as ELISA assays, to detect FIPV infection.

EXAMPLE 5

ELISA Assay

In order to test various cat sera for their reactivity to the 7B-MBP construct, an ELISA assay was employed. Briefly, 7B-MBP, and MBP protein only, were coated at 50 μg/ml on duplicate plates using Carbonate coating buffer pH 9.6 overnight. Plates were washed with PBS/Tween 3×, and cat sera applied. Each sera was diluted in blocking buffer (PBS/Tween with 500 μg/ml MBP) and applied to coated wells for 1 hour at 37° C. Plates were washed with PBS/Tween, and an anti-cat IgG biotin conjugated monoclonal (Sigma) added (1:1000) for 1 hour at room temp. After washing, Extravidin/Alkaline (Sigma) phosphatase conjugate at 1:1000 in PBS/Tween was added for 30 minutes at room temp; after a final washing step, plates were developed with nitrophenylphosphate substrate (Sigma).

EXAMPLE 5

Specificity of ELISA Based Assays

An ELISA immunoassay for determining prior infection with FIPV using the 7B-maltose binding protein fusion protein was conducted to measure the specificity of the assay. The assay uses microwell plates coated with 10 μg/ml of the 7B-maltose binding protein fusion protein. Cat sera were diluted 1:40 and incubated for one hour in the coated wells. After washing, the wells were subsequently incubated with biotin labeled anti cat-IgG. The assay was completed with standard methods for the development of a colorimetric response and quantitated on a microplate reader. Each of the sera was similarly assayed in control wells that were coated with MBP only. Results are presented in Table II below.

Table II demonstrates that after subtracting out the background signal in the maltose binding protein control, only three cats, Nos. 35, 45 and 51, had significant antibody titers against the 7B peptide fragment. Thus, the ELISA based assay selectively and specifically detects cats which have been exposed to FIPV.

TABLE II

ELISA FOR ANTIBODY AGAINST 7B ANTIGEN IN THE SERA OF FIP SUSPECT CATS

| Cat No. | O.D. 7B–MBP | O.D. MBP only | Δ O.D. |
|---|---|---|---|
| 033 | −.039 | −.043 | 0.004 |
| 034 | −.050 | 0.007 | 0.043 |
| 035 | 0.328 | 0.021 | 0.307 |
| 036 | 0.007 | 0.037 | 0.030 |
| 037 | −0.020 | −0.015 | −0.005 |
| 038 | −0.015 | 0.057 | −0.072 |
| 039 | −0.033 | 0.047 | −0.080 |
| 040 | −0.047 | −0.016 | −0.031 |
| 041 | −0.009 | −0.047 | 0.038 |
| 042 | 0.013 | −0.027 | 0.040 |
| 043 | −0.054 | −0.072 | 0.018 |
| 044 | −0.033 | −0.027 | −0.006 |
| 045 | 0.217 | −0.029 | 0.246 |
| 046 | 0.055 | 0.057 | −0.002 |
| 047 | −0.009 | 0.019 | −0.028 |
| 048 | 0.085 | 0.127 | −0.042 |
| 049 | −0.030 | −0.032 | 0.002 |
| 050 | −0.020 | −0.036 | 0.016 |
| 051 | 0.0210 | −0.038 | 0.243 |

EXAMPLE 6

ELISA Based Assays Detect Cats Known to be Infected With FIPV

The data in Table III below were obtained in a survey of a cattery in which FIP was endemic ("The Chicago Cattery"). An ELISA assay similar to that described above was conducted except that it was adjusted to give a higher signal-to-noise ratio.

The results obtained with the ELISA assay were compared to those obtained by PCR (compare columns 4 and 5 of Table III). This comparison shows that cats known to be infected with FIPV as determined by PCR, yield the highest signals in the ELISA (mean specific OD >1.4635, n=8, range 0.790→1.805). In contrast, cats which do not yield an amplified fragment in the PCR assay have a mean specific O.D. of 0.347 (n=27, S.D.=0.48506., range 0.0→1.301). Of the cats yielding negative results in only 5 cats have a specific O.D. greater than the values for the PCR positive cats. It is possible that these 5 cats are infected with FIPV but that the PCR assay did not detect the infection as a result of the limitations of the PCR assay discussed above. These results clearly indicate the utility of the diagnostic for detecting FIPV-infected cats since minimally 8/13 cats would have been detected as being infected with FIPV if the lowest specific O.D. for known infected cats had been chosen as a cut-off.

TABLE III

COMPARISON OF 7B-BASED ELISA WITH PCR-BASED DIAGNOSIS FOR FIPV

| Cat No. | O.D. 7B–MBP | O.D. MBP only | Δ O.D. | FIPV + by PCR |
|---|---|---|---|---|
| 1 | 0.227 | 0.157 | 0.070 | |
| 2 | >2.0 | 0.291 | >1.709 | +++ |
| 3 | 0.242 | −0.001 | 0.243 | |

TABLE III-continued

COMPARISON OF 7B-BASED ELISA
WITH PCR-BASED DIAGNOSIS FOR FIPV

| Cat No. | O.D. 7B–MBP | O.D. MBP only | Δ O.D. | FIPV + by PCR |
|---|---|---|---|---|
| 4 | 0.644 | 0.312 | 0.332 | |
| 5 | 0.621 | 0.597 | 0.024 | |
| 6 | −0.015 | 0.077 | −0.092 | |
| 7 | 0.008 | 0.739 | −0.731 | |
| 8 | >2.0 | 0.195 | >1.805 | +++ |
| 9 | 0.908 | 0.104 | 0.804 | |
| 10 | 1.303 | 0.644 | 0.659 | |
| 11 | >2.0 | 1.119 | >0.881 | |
| 12 | 0.284 | 0.117 | 0.167 | |
| 13 | >2.0 | 0.532 | >1.468 | +++ |
| 14 | 0.564 | 0.249 | 0.315 | |
| 15 | 0.025 | 0.548 | −0.523 | |
| 16 | 0.124 | 0.329 | −0.205 | |
| 17 | 1.058 | 0.268 | 0.790 | +++ |
| 18 | >2.0 | 0.336 | >1.664 | +++ |
| 19 | 1.108 | 0.209 | 0.899 | +++ |
| 20 | >2.0 | 0.699 | >1.301 | |
| 21 | 0.732 | 0.111 | 0.0621 | |
| 22 | 0.876 | 0.219 | 0.657 | |
| 23 | 0.772 | 0.265 | 0.507 | |
| 24 | 0.548 | 0.899 | −0.351 | |
| 25 | 0.487 | 0.448 | 0.039 | |
| 26 | 0.984 | 0.143 | 0.841 | |
| 27 | >2.0 | 0.336 | >1.664 | +++ |
| 28 | 1.474 | 0.967 | 0.507 | |
| 29 | 1.154 | 0.153 | 1.001 | |
| 30 | 0.185 | 0.043 | 0.142 | |
| 31 | 1.030 | 0.124 | 0.906 | |
| 32 | 0.614 | 0.481 | 0.133 | |
| 33 | >2.0 | 0.291 | >1.709 | +++ |
| 34 | 0.688 | 0.058 | 0.630 | |
| 35 | 0.845 | 0.366 | 0.479 | |
| 36 | 0.487 | 0.177 | 0.310 | |
| 37 | 1.002 | 0.238 | 0.764 | |
| 38 | 0.732 | 0.357 | 0.375 | |
| 39 | 1.413 | 0.388 | 1.025 | |
| 40 | 0.341 | 0.071 | 0.270 | |

A further study was conducted using the above assay on cat sera from cats that had either tested positive or negative for FIPV infection by PCR analysis. The results, shown in FIG. 5, show that over a range of three different dilutions of sera, PCR positive cats are clearly distinguishable from PCR negative cats. In particular at a dilution of 1;400, the Pcr negative cat sera produced an ELISA signal of nearly zero, while the weakest ELISA signal for a PCR positive cat was O.D.$_{405}$=0.3.

EXAMPLE 7

Correlation Between High Titers of Antibodies Against the Unique Peptide Measured by ELISA and Detection of FIPV Nucleic Acid by PCR A further study was made using the same assay on cat sera from cats that had either tested positive or negative for FIPV infection using a PCR diagnostic. These results are shown in graphically in FIG. 6. It shows that over a range of three different dilutions of the sera, that the PCR positive cats are clearly distinguishable from the PCR negative cats. In particular, at a dilution of 1:400, the PCR negative cat sera had ELISA readings that were almost zero, while the weakest ELISA signal for the PCR positive cat sera was at approximately 0.3 O.D.

The diagnostic described in this invention permits the true diagnosis of cats that have become infected with FIPV. The utility of this information is that it permits rational decisions regarding the management of cats that are infected with FIPV and which, because of this status, represent a possible threat for the fatal infection of other cats not so infected.

EXAMPLE 9

Preparation of Polyclonal Antibodies Against the Unique 7B Fragment

The 7B-maltose binding protein fusion protein is purified from host cells containing the pMAL 7B-maltose binding protein fusion vector as described above.

For the production of polyclonal antibodies, the protein is emulsified in Freunds complete adjuvant and up to 10 μg of protein is injected into rabbits. After two booster shots of the lysed membranes, the rabbits are bled and the sera isolated by centrifugation.

The antibodies in the crude rabbit sera extract are $^{125}$I labeled by well-known methods and tested for activity against the 7B-maltose binding protein fusion protein in Western blots as described above.

Monoclonal antibodies can be made by well known methods in addition to the polyclonal antibodies discussed above. One method of producing monoclonal antibodies is discussed below.

EXAMPLE 10

Production of Monoclonal Antibodies Against the Unique 7B Peptide

The 7B-maltose binding protein fusion protein is purified from cells containing the pMAL 7B-maltose binding protein expression vector as described above. Fractions containing the 7B-maltose binding protein fusion protein are injected in Freunds adjuvant into mice. After being injected 9 times over a three week period, the mice spleens are removed and following conventional cell separation techniques are resuspended in PBS.

The suspended spleen cells are mixed (approximately 4:1) with SP 2/0 Myeloma cells. Polyethylene glycol is added to fuse the myeloma cells to the spleen cells, and the fused cells are selected in HAT media. The fused cells are aliquoted so that only one cell is grown in each well of a 96-well microtiter plate. Each cell is grown, the media removed and secreted proteins in the media are $^{125}$I or fluorescently labeled. The labeled media from each well is used in a Western blot of a gel on which the 7B-maltose binding protein fusion protein has been run. The desired fusion cell will produce a monoclonal antibody that strongly binds the 7B-maltose binding protein fusion protein on the Western blot, but doesn't bind to a maltose binding protein control.

The antibodies prepared according to Examples 9 or 10 can then be used in ELISA assays as described above to detect the presence of the 7B protein in samples from cats potentially infected with FIPV. Alternatively, the antibodies prepared as above may be used in radioimmunoassays such as those described below to detect the presence of the unique 7B peptide in a sample.

EXAMPLE 11

Radioimmunoassays

The 7B-maltose binding protein is labelled using standard techniques such as those disclosed in Sambrook et al., *Molecular Cloning: A Laboratory Manual*, Cold Spring Harbor Press, (1989). The labelled 7B-maltose binding protein is mixed with antibodies prepared as described above in Examples 9 or 10. The antibodies may be linked to beads using techniques well known to those skilled in the art. Alternatively, the antibodies may be free in solution.

Various dilutions of sera from cats being tested for FIPV infection are added to the 7B-maltose binding protein/antibody mixture. The samples are incubated and the amount of labelled 7B-maltose binding protein bound to the antibodies is quantitated using standard techniques. The amount of radioactive 7B-maltose binding protein precipitated in samples to which sera has been added is compared to a control sample to which no sera was added. A significant reduction in the amount of bound 7B-maltose binding protein in the sera containing sample relative to the control indicates that the unique 7B peptide is present in the sample and the animal tested is infected with FIPV.

EXAMPLE 12

PCR based Diagnostics Exploiting the Sequence Differences between Applicant's Sequence and the Published Sequence The DNA sequence differences between Applicant's unique 7B sequence and the published unique 7B sequence may be exploited in improved PCR diagnostics to detect organisms infected with Feline Infectious Peritonitis Virus. These improved PCR based diagnostics have enhanced detection rates.

A DNA sample is obtained from the organism to be tested. A PCR amplification reaction is performed on the DNA sample in which at least one of the primers comprises a sequence contained within SEQ ID NO:2. The at least one primer has at least one nucleotide which differs between SEQ ID NO:2 and SEQ ID NO: 1.

Alternatively, both primers used in the amplification comprise a sequence contained within SEQ ID NO:2 in which at least one nucleotide of each primer differs between SEQ ID NO:2 and SEQ ID NO:1. For example, the primers used in the PCR diagnostic may have the sequences of SEQ ID NO: 5 and SEQ ID NO:6.

The presence of an amplified fragment after the PCR reaction indicates that the organism is infected with Feline Infectious Peritonitis Virus.

While particular embodiments of the invention have been described in detail, it will be apparent to those skilled in the art that these embodiments are exemplary rather than limiting, and the true scope of the invention is that defined in the following claims. Those skilled in the art will appreciate that the antigenicity of the unique 7B polypeptide can be exploited to detect FIPV infection using a variety of other well known immunological techniques. For example, the unique 7B polypeptide can be fixed to supports other than microtiter plates, such as dipsticks, chromatography materials, or beads.

The 7B polypeptide may also be used in a vaccine to induce protective immunity in animals, as described in Example 13 below.

EXAMPLE 13

Use of the 7B Protein in Vaccines

The 7B protein may be used as a vaccine to induce an immune response against FIPV in animals such as cats. Preferably, the induced immune response is a protective immune response.

In such procedures, the 7B protein, or a portion thereof containing at least one antigenic epitope, is expressed from an expression vector such as the expression vectors described in Example 2. If desired, the expressed 7B protein or portion thereof used in the vaccine may be purified using the techniques of Example 2 or other conventional protein purification techniques.

The 7B protein or portion thereof used in the vaccine may comprise at least 10 consecutive amino acids of the 7B protein. The 7B protein or portion thereof may comprise the 7B proteins of strain 79-1146 (which includes SEQ ID NO:3), the 7B protein or portion thereof from the FIPV strain disclosed by applicant herein (which includes SEQ ID NO:4) or the 7B protein or portion thereof from any FIPV strain. The sequences of the 7B proteins of several FIPV strains are disclosed in Herrewegh et al., The Molecular Genetics of Feline Coronaviruses: Comparative Sequence Analysis of the ORF7a/7b Transcription Unit of Different Biotypes, Virology 212:622–631 (1995), the disclosure of which is incorporated herein by reference. Preferably, the 7B protein or portion thereof used in the vaccine comprises at least 15 consecutive amino acids of the 7B protein. In some embodiments, the 7B protein or portion thereof used in the vaccine may comprise at least 20 consecutive amino acids of the 7B protein. In still other embodiments the 7B protein or portion thereof used in the vaccine comprises more than 20 consecutive amino acids of the 7B protein. The 7B protein or portion thereof used in the vaccine may comprise the entire unique 7B protein. Alternatively, the 7B protein or portion thereof used in the vaccine may comprise the entire 7B protein.

In some embodiments, the 7B protein or portion thereof used in the vaccine comprises the 7B protein of SEQ ID NO:4 or a portion thereof. The 7B protein or portion thereof used in the vaccine may comprise at least 10 consecutive amino acids of the 7B protein of SEQ ID NO:4. Preferably, the 7B protein or portion thereof used in the vaccine comprises at least 15 consecutive amino acids of the 7B protein of SEQ ID NO:4. In some embodiments, the 7B protein or portion thereof used in the vaccine may comprise at least 20 consecutive amino acids of the 7B protein of SEQ ID NO:4. In still other embodiments the 7B protein or portion thereof used in the vaccine comprises more than 20 consecutive amino acids of the 7B protein of SEQ ID NO:4. The 7B protein or portion thereof used in the vaccine may comprise the entire unique 7B protein of SEQ ID NO:4. Alternatively, the 7B protein or portion thereof used in the vaccine may comprise the entire 7B protein which contains the sequence of SEQ ID NO:4 therein.

The antigenicity of the 7B proteins or portions thereof to be used in the vaccines may be evaluated as follows. The 7B proteins or portions thereof are administered to an animal in a pharmaceutically acceptable carrier using conventional methods. If desired, the 7B proteins or portions thereof may be administered along with an adjuvant, such as Freund's Incomplete Adjuvant or aluminum hydroxide. If desired, the 7B protein or portion thereof may be coupled to a hapten.

The 7B protein or portion thereof may be administered one time or several times. After completion of the administration regimen, serum is prepared from the animal and assayed for the presence of antibodies against the 7B protein or portion thereof using ELISA assays or T cell stimulation assays such as those described above or other conventional techniques.

Appropriate doses of the 7B protein or portion thereof sufficient to induce an immune response are evaluated as follows. The titer of the antibodies in animals receiving varying doses of 7B protein or portion thereof is determined using the methods described in antigenicity analyses above or other conventional titering methods. Alternatively, appropriate doses may be determined by challenging animals with FIPV.

In such challenge analyses, the 7B protein or portion thereof is administered to an animal using conventional techniques. Preferably, the 7B protein or portion thereof is administered with an adjuvant such as Freund's Incomplete Adjuvant or aluminum hydroxide. The 7B protein or portion thereof may be administered once or several times in varying doses. Serum levels of antibodies against the 7B protein or polypeptide are evaluated using ELISA analyses such as those described above. Once antibody levels likely to confer a desired level of immune response are observed, the vaccinated animals, along with unvaccinated control animals, are challenged twice with a virulent strain of FIPV using methods such as those disclosed in Pedersen, N and Black J. W., Attempted Immunization of Cats Against Feline Infectious Peritonitis Using Avirulent Live Virus or Sublethal Amounts of Virulent Virus, Am. J. Vet. Res. 44: 229–234 (1983), the disclosure of which is incorporated by reference. Preferably, the desired level of immune response is a protective immune response.

Once protective doses of the 7B protein or portions thereof have been determined a desired level of immune response against FIPV may be obtained by administering a dose of the 7B protein or portion thereof sufficient to confer the desired level of immune response as determined using the methods above. Preferably, the dose of 7B protein administered to the animals is sufficient to confer a protective immune response.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims. All documents cited herein are incorporated herein by reference in their entirety.

What is claimed is:

1. A method for determining whether a mammal is infected with Feline Infectious Peritonitis Virus (FIPV) comprising the steps of:
    providing a peptide or polypeptide including at least one antigenic site from the unique 7B polypeptide therein;
    contacting said peptide or polypeptide with serum containing antibodies from said mammal;
    determining whether said antibodies in said serum bind to said peptide or polypeptide, whereby detection of binding of said antibodies to said peptide or polypeptide indicates that the mammal is infected with Feline Infectious Peritonitis Virus.

2. The method of claim 1, wherein said peptide or polypeptide includes at least one antigenic site from SEQ. ID. NO: 4 therein.

3. The method of claim 2, wherein said determining step comprises contacting said antibodies from said serum with a second antibody, said second antibody being capable of providing a detectable signal, wherein the presence of said signal indicates the presence of antibodies directed against said peptide or polypeptide in said serum.

4. The method of claim 3, wherein said second antibody is linked to an enzyme capable of providing a detectable signal.

5. The method of claim 3, wherein said second antibody is labelled with a radioactive isotope.

6. The method of claim 1, wherein said peptide or polypeptide is coated on a surface.

7. The method of claim 6, wherein the surface is a microtiter plate.

8. The method of claim 1, wherein said mammal is a feline.

9. A method of detecting the presence of antibodies in a mammal directed against a peptide or polypeptide comprising at least one antigenic site from the sequence of SEQ ID NO:4 therein, said method comprising:
    labeling said peptide or polypeptide;
    contacting said peptide or polypeptide with an antibody directed against an antigenic site from SEQ ID NO:4;
    adding varying amounts of sera from said mammal to said labeled peptide or polypeptide and said antibody;
    detecting and quantitating the amount of labeled peptide or polypeptide bound to said antibody in said samples; and
    comparing the amount of labeled peptide or polypeptide bound to said antibody in said samples containing varying amounts of said serum to the amount of labeled peptide or polypeptide bound to said antibody in a control sample lacking the 7B protein, wherein decreased binding in said samples containing said serum relative to said control sample indicates the presence of antibodies against a peptide or polypeptide containing an antigenic site from the sequence of SEQ ID NO:4 in said serum.

10. The method of claim 9, wherein said mammal is a feline.

11. The method of claim 9, wherein said peptide or polypeptide is labeled radioactively.

12. The method of claim 9, wherein said antibody is a monoclonal antibody.

13. A diagnostic assay kit comprising:
    a polypeptide bound to a solid support matrix, wherein said polypeptide specifically binds with antibodies against the polypeptide comprising the amino acid sequence of SEQ ID NO:4 but does not specifically bind with antibodies against Feline Enteric Coronavirus (FECV).

14. The diagnostic assay kit according to claim 13, wherein said polypeptide comprises the amino acid sequence of SEQ ID NO:4.

15. The diagnostic assay kit according to claim 13, further comprising a detectable label that binds to said antibodies.

16. The diagnostic assay kit according to claim 15, wherein said detectable label is a Protein-A colloidal gold conjugate.

17. A method of detecting the presence of antibodies in a mammal directed against a peptide or polypeptide comprising at least one antigenic site from the sequence of SEQ ID NO:4 therein, said method comprising:
    adding varying amounts of sera from said mammal to a mixture comprising labeled peptide or polypeptide and an antibody directed against an antigenic site from SEQ ID NO: 4;
    detecting and quantitating the amount of labeled peptide or polypeptide bound to said antibody in said samples; and
    comparing the amount of labeled peptide or polytide or polypeptide bound to said antibody in said samples containing varying amounts of said serum to the amount of labeled peptide or polypeptide bound to said antibody in a control sample lacking the 7B protein, wherein decreased binding in said samples containing said serum relative to said control sample indicates the presence of antibodies against a peptide or polypeptide containing an antigenic site from the sequence of SEQ ID NO:4 in said serum.

* * * * *

```
                            SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
          (A) LENGTH: 238 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:1:

TGTTGGTTGT CATACATCAT TTGCTGTTGA TCTTCCATTT GGGATTCAGA TATACCATGA        60

CAGGGATTTT CAACACCCTG TTGATGGCAG ACATCTAGAT TGTACTCACA GAGTGTACTT      120

TGTGAAGTAC TGTCCACATA ACCTGCATGG TTATTGCTTT AATGAGAGGC TGAAAGTTTA      180

TGACTTGAAG CAATTCAGAA GCAAGAAGGT CTTCGACAAA ATCAACCAAC ATCATAAA       238

(2) INFORMATION FOR SEQ ID NO:2:

(i) SEQUENCE CHARACTERISTICS:
          (A) LENGTH: 238 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:2:

TGTTGGTTGT CATACATCAT TTGCTGTCGA CCTTCCATTT GGAACTCAGA TTTACCATGA        60

CAGGGATTTC CAAAACCCTG TTAATGGTAG GCATCTAGAG TGTACTCACA GAGTTTACTT      120

TGTGAAGTAC TGTCCATACA ACCTGCATGG TTATTGCTTT AATGAGAAGC TGAAAGTTCA      180

TAACTTGATG CAACTTAGAA GCAAGAAGGT TTTTGACAAG ATCAACCAAC ATCATTAA       238

(2) INFORMATION FOR SEQ ID NO:3:
```

(i) SEQUENCE CHARACTERISTICS:
    (A) LENGTH: 79 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:3:

Val Gly Cys His Thr Ser Phe Ala Val Asp Leu Pro Phe Gly Ile Gln
1               5                   10                  15

Ile Tyr His Asp Arg Asp Phe Gln His Pro Val Asp Gly Arg His Leu
            20                  25                  30

Asp Cys Thr His Arg Val Tyr Phe Val Lys Tyr Cys Pro His Asn Leu
        35                  40                  45

His Gly Tyr Cys Phe Asn Glu Arg Leu Lys Val Tyr Asp Leu Lys Gln
    50                  55                  60

Phe Arg Ser Lys Lys Val Phe Asp Lys Ile Asn Gln His His Lys
65                  70                  75

(2) INFORMATION FOR SEQ ID NO:4:

(i) SEQUENCE CHARACTERISTICS:
        (A) LENGTH: 78 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Val Gly Cys His Thr Ser Phe Ala Val Asp Leu Pro Phe Gly Thr Gln
1               5                   10                  15

Ile Tyr His Asp Glu Asp Phe Gln Asn Pro Val Asn Gly Arg His Leu
            20                  25                  30

Glu Cys Thr His Arg Val Tyr Phe Val Lys Tyr Cys Pro Tyr Asn Leu
        35                  40                  45

His Gly Tyr Cys Phe Asn Glu Lys Leu Lys Val His Asn Leu Met Gln
    50                  55                  60

Leu Arg Ser Lys Lys Val Phe Asp Lys Ile Asn Gln His His
65                  70                  75

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

TGTTGGTTGT CATACATCAT TTG                                    23

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear -continued (ii) MOLECULE TYPE: cDNA (xi) SEQUENCE DESCRIPTION: SEQ ID NO:6:

CTCAGTTTAA TGATGTTGGT TG					22